United States Patent [19]

Bade

[11] Patent Number: 4,832,871

[45] Date of Patent: May 23, 1989

[54] METHOD FOR THE PREPARATION OF A HIGHLY CONCENTRATED, FLOWABLE AND PUMPABLE BETAINE SOLUTION

[75] Inventor: Volkbert Bade, Essen, Fed. Rep. of Germany

[73] Assignee: Th. Goldschmidt AG, Essen, Fed. Rep. of Germany

[21] Appl. No.: 38,731

[22] Filed: Apr. 15, 1987

[30] Foreign Application Priority Data

Apr. 24, 1986 [DE] Fed. Rep. of Germany ....... 3613944

[51] Int. Cl.$^4$ ................. C07C 101/00; C07C 103/00; C11D 1/00; C11D 3/26
[52] U.S. Cl. ............................. 252/546; 260/404.5; 260/501.13; 252/153; 252/356; 252/357; 252/DIG. 5; 252/DIG. 13
[58] Field of Search ............. 260/404.5 R, 404.5 Q, 260/501.13; 252/DIG. 5, DIG. 7, DIG. 13, 546, 541, 153, 547, 356, 357

[56] References Cited

U.S. PATENT DOCUMENTS

| | | | |
|---|---|---|---|
| 3,366,671 | 1/1968 | Conan et al. | 260/404.5 |
| 3,912,662 | 10/1975 | Martinsson et al. | 252/153 |
| 4,137,191 | 1/1979 | Lohr | 252/DIG. 5 |
| 4,243,549 | 1/1981 | Messenger et al. | 252/153 |
| 4,246,131 | 1/1981 | Lohr | 252/153 |
| 4,299,740 | 11/1981 | Messenger et al. | 252/541 |
| 4,497,825 | 5/1985 | Bade | 260/501.13 |

FOREIGN PATENT DOCUMENTS

3613944  8/1987  Fed. Rep. of Germany ............ 260/501.13
2023637  1/1980  United Kingdom ............... 252/547

*Primary Examiner*—Patrick P. Garvin
*Assistant Examiner*—K. D. Irzinski
*Attorney, Agent, or Firm*—Toren, McGeady & Associates

[57] ABSTRACT

A method is disclosed for the preparation of a flowable and pumpable solution containing at least 70 weight percent of betaine of the following general formula

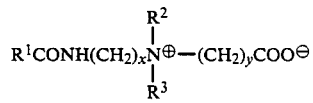

in which $R^1$ is the alkyl group of a fatty acid or a fatty acid mixture with an average of 6 to 18 carbon atoms, $R^2$ and $R^3$ are the same or different and represent an alkyl or a hydroxyalkyl group with 1 to 4 carbon atoms, x has a value of 2 or 3 and y a value of 1,2,3 or 4.

The solutions prepared by the method have a viscosity of not more than 25,000 mPas at 25° C., as a result of which the compounding of the solutions to liquid soaps, shampoos, shower gels and other cosmetic preparations is facilitated, while at the same time the costs of dispensing, transporting and warehousing are reduced. Solutions containing at least 70 percent by weight of the above betaines are also disclosed.

10 Claims, No Drawings

METHOD FOR THE PREPARATION OF A HIGHLY CONCENTRATED, FLOWABLE AND PUMPABLE BETAINE SOLUTION

FIELD OF INVENTION

The invention generally relates to betaines and is particularly directed to a method for the preparation of a flowable and pumpable solution, which contains at least 70 weight percent of a betaine of the general formula

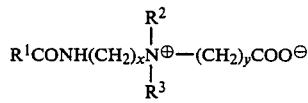  I in which $R^1$ is the alkyl group of a fatty acid or a fatty acid mixture with an average of 6 to 18 carbon atoms, $R^2$ and $R^3$ are the same or different and represent an alkyl or a hydroxyalkyl group with 1 to 4 carbon atoms, x has a value of 2 or 3 and y a value of 1, 2, 3 or 4, by the quaternization of a compound of the general formula $R^1CONH(CH_2)_xNR^2R^3$ with the salt of a halogencarboxylic acid $X(CH_2)_yCOOMe$, in which X is halogen and Me a monovalent cation, at elevated temperatures. Considered from another aspect, the invention is also concerned with concentrated betaine solutions containing at least 70 percent by weight of betaine of formula I.

BACKGROUND INFORMATION AND PRIOR ART

Betaines of the above-named formula have gained increasing importance in past years for the preparation of body cleansing and personal care agents. They combine excellent cleansing properties with good skin tolerance. In aqueous solution, the betaines form a stable, dense foam, which does not collapse even in the presence of soap.

The synthesis of such betaines is described in many patents, of which U.S. Pat. No. 3,225,074 is cited as representative. In general, the corresponding tertiary fatty acid amidamine is reacted with the alkali salt of a halogencarboxylic acid, usually chloroacetic acid. The reaction takes place in an aqueous medium. The alkali chloride, formed by the reaction, is left in this aqueous betaine solution. Such betaines are therefore generally marketed at a concentration of about 30 weight percent in the form of aqueous or alkaline aqueous solutions.

There has been no lack of attempts to prepare more concentrated solutions of the betaines, in order to reduce the costs of the transport and storage of the betaine solutions.

The expert knows that the viscosity of an aqueous surfactant solution also increases as the concentration increases. Frequently, however, it turns out that, when the concentration exceeds a value of about 60 to 70 weight percent, the viscosity decreases to a minimum with further increases in concentration and then rises again steeply. To explain this viscosity anomaly, it is assumed that a phase (the so-called G phase) with a lamellar structure is formed in the solution. This decrease in the viscosity of surfactant solutions at a concentration of about 60 to 70 weight percent is utilized for the preparation of highly concentrated surfactant solutions and is described, for example, in "Soap, Perfumery, Cosmetics", 1982, 507 to 509.

This viscosity anomaly also forms the background for the method of the German Patent No. 2,557,456, in which, for the synthesis of amine oxides by the oxidation of amines in the presence of water, such an amount of water is added, that the water concentration in the product mixture is 20 to 30 weight percent. In this method, efforts thus are already made during the synthesis to attain a surfactant solution, which corresponds to the viscosity minimum at high concentrations.

If water is removed from betaine solutions obtained in the usual manner, the viscosity of these solutions increases. However, at a concentration of about 40 weight percent betaine, the solution become pasty and increasingly solid as further water is removed.

Liquefaction on drying the solid product further has not been observed. Therefore, according to the state of the art, it was not possible to obtain highly concentrated solutions, which contain at least 70 weight percent of betaine of the general formula I and which are still flowable and can be metered, for example, with pumps.

OBJECTS OF THE INVENTION

It is a primary object of the invention to provide flowable and pumpable betaine solutions containing at least 70 weight percent of betaine, so as to lower therewithin the dispensing, transporting and warehousing costs and to facilitate the compounding into liquid soaps, shampoos, shower gels or other cosmetic preparations. It is a particular object of the invention to provide betaine solutions, which contain at least 70 weight percent of betaine and have a viscosity not greater than 25,000 mPas at 25° C.

It is also an object of the invention to provide a method for preparing concentrated betaine solutions. Generally, it is an object of the invention to improve on the art of manufacturing betaine solutions.

SUMMARY OF INVENTION

Surprisingly, it was discovered in accordance with this invention that, starting from the known procedures, these objects can be superiorly accomplished by proceeding as follows:

(a) the $R^1$ group is selected so that the compound of the formula $R^1CONH(CH_2)_xNR^2R^3$ has a melting point no higher than 30° C., (b) the quaternization is carried out (b₁) with the potassium or ammonium salt of the halogencarboxylic acid $X(CH_2)_yCOOH$, wherein the salt may be prepared in situ;

(b₂) in a polar organic solvent, which must not contain more than 20 weight percent of water, (c) after the quaternization, the water that may be present is distilled off azeotropically and the precipitated potassium or ammonium halides is removed, (d) the solvent is then distilled off partly or completely and (e) before, simultaneously with or after the distillation, the concentration of the betaine in the solvent or the solvent mixture required for the application is adjusted to the desired value.

Characteristic (a) relates to the selection of the suitable tertiary amines for the betaine that is to be synthesized for use in the inventive procedure. It has been ascertained that flowable and pumpable, highly concentrated betaine solutions are obtained only if the melting point of the tertiary amines of the formula $R^1CONH(CH_2)_xNR^2R^3$ is no higher than 30° C. The melting point of the tertiary amines, moreover, depends essentially on the fatty acid $R^1COOH$ or of the corresponding fatty acid mixture used for the synthesis of the tertiary amines. The longer the chain of the fatty acid, the higher is the melting point of the tertiary amine. If essentially pure, homogeneous fatty acids are used for the synthesis of the tertiary amine of the above formula, the number of their carbon atoms should not exceed 10. A melting point depression is observed when a mixture of fatty acid is used. It is therefore possible to use mixtures of fatty acids, the average chain length of which is greater than that of pure, homogeneous fatty acids. For example, fatty acid mixtures, obtained from hydrogenated (hardened) coconut fat and having an average of about 12 carbon atoms, have proven to be useful. Monounsaturated and polyunsaturated fatty acids are also suitable for the synthesis of tertiary amines that are to be used for the inventive method.

Examples of suitable fatty acids accordingly are the saturated fatty acids with 6 to 10 carbon atoms, such as $C_5H_{11}COOH$ (caproic acid), $C_7H_{15}COOH$ (caprylic acid) and $C_9H_{19}COOH$ (capric acid), mixtures of saturated fatty acids with up to 12 carbon atoms on the average, unsaturated fatty acids such as oleic acid, linoleic acid, recinoleic acid or their mixtures with saturated fatty acids.

Characteristic (b) relates to the quaternization reaction. The quaternization is accomplished with the potassium or ammonium salt of the halogencarboxylic acid $X(CH_2)_yCOOH$. Moreover, the potassium or ammonium salt may be produced in situ. The quaternization is carried out in a polar, organic solvent. In this connection it is of considerable importance that the solvent contains no more than 20 weight percent of water.

As polar, organic solvent, aliphatic alcohols with 2 to 4 carbon atoms, such as ethanol, propanol, butanol and particularly isopropanol are especially suitable.

Corresponding to characteristic (c) of the inventive method, the water that may be present after the quaternization reaction is distilled off azeotropically. The precipitated ammonium or potassium halide is removed from the reaction product. This can be done appropriately by filtering or centrifuging.

A solution of the desired betaine in the polar, organic solvent is obtained, which may, however, still contain certain residual amounts of ammonium or potassium halide. Removal of the residual amount of the salt, which may amount to about 2 to 5 weight percent, is not necessary.

To convert the solution of the betaine of formula I, so obtained in the polar organic solvent used, into a solution, which contains the solvent or solvent mixture required for the application, the polar organic solvent is now distilled off and, before, simultaneously with or after the distillation, the concentration of the betaine is adjusted to the desired value in the solvent or solvent mixture required for the application. If the solution aimed for and required for the application is to contain small amounts of the alcohol used for the reaction, the solvent is distilled off only to the extent that it exceeds this amount. The solvents, desirable for the applications, are especially the aliphatic diols with 2 to 4 carbon atoms, such as ethylene glycol, propylene glycol or butylene glycol. Propylene glycol is especially preferred.

Preferably, the required amount of diol is added to the solution of the betaine in the polar organic solvent and the polar organic solvent is distilled off. A solution of the betaine in the desired solvent is obtained, the concentration of the betaine being adjusted by the amount of solvent, such as propylene glycol, that is added.

A further correction to the viscosity of the betaine solution obtained can be made by adding aliphatic alcohols with 2 to 4 carbon atoms, preferably ethanol, and optionally small amounts of water to the solution so obtained. The alcohol may be added in amounts of 0.5 to 10 weight percent and the water in amounts of up to 5 weight percent, based on the total weight of the preparation. If this alcohol is identical with the alcohol chosen as reaction medium, the amount is taken into consideration in step (d) of the method.

The aliphatic diol, alcohol and optionally water are advisably added up to a final concentration of
70 to 97.5 weight percent betaine
2 to 15 weight percent aliphatic diol
0.5 to 10 weight percent ethanol
0 to 5 weight percent water.

Knowing the state of the art, it was not foreseeable that, by adhering to the conditions of the method of the invention, flowable and pumpable, highly concentrated betaine solutions could be prepared. These concentrated solutions can be dispensed, transported and processed particularly economically.

The concentrated solutions of the betaines provided pursuant to the invention have the following composition:
70 to 97.5 weight percent betaine of formula I
2 to 15 weight percent aliphatic dialcohol with 2 to 4 carbon atoms
0.5 to 10 weight percent aliphatic monoalcohol with 2 to 4 carbon atoms, and
0 to 5 weight percent water.

Especially preferred are solutions of the composition:
70 to 97.5 weight percent betaine of formula I
2 to 15 weight percent propylene glycol
0.5 to 10 weight percent ethanol
0 to 5 weight percent water.

The method of the invention is described in greater detail in the following examples, it being understood that these examples are given by way of illustration and not by way of limitation.

EXAMPLE 1

The dimethylaminopropylamide of hydrogenated (hardened) coconut oil fatty acids (600 g), 220 g of chloroacetic acid and 800 g of isopropanol are added to a 2 L glass flask, which is equipped, with a stirrer, thermometer, reflux condenser and gas inlet tube.

The reaction mixture is heated slowly with stirring to 95° to 98° C. At the same time, ammonia gas is passed into the mixture in an amount of 10 to 15 L/hour through the gas inlet tube. After about 60 minutes, cloudiness develops due to the precipitation of the ammonium chloride. After a total reaction time of about 4 hours, the addition of the ammonia gas is reduced to less than 5 L/hour and the reaction is continued until the concentration of starting amide used has fallen below 3 weight percent. The reaction mixture is then cooled to room temperature and the precipitated ammonium chloride is filtered off. A total of 78.9 g of dry ammonium chloride is obtained, corresponding to 65% of the theoretically possible amount.

The filtrate of 1574 g has a solids content of 49.6 weight percent and is referred to as product A.

Product A (1574 g) is mixed with 138 g of 1,2-propyleneglycol and subsequently freed from isopropanol by vacuum distillation. After cooling to 50° C., the reaction product (918.5 g) is mixed with 19 g of ethanol and cooled to 30° to 40° C. At this temperature, 4 g of NaClO₂ (15% solution in water) are added for bleaching.

The final product has a viscosity of 20,000 mPas at room temperature, a Hess-Ives color number of 2 and the following composition: 78.8 weight percent betaine, 4.6 weight percent ammonium chloride, 14.6 weight percent propylene glycol, 2.0 weight percent ethanol.

EXAMPLE 2

Product A of Example 1 (1,000 g) is mixed with 71.7 g of 1,2-propyleneglycol. Isopropanol is distilled off and 30 g of ethanol is added to the residue. The product has a viscosity of approximately 10,000 mPas, a Hess-Ives color number of 2 and the following composition: 78.4 weight percent betaine, 4.6 weight percent ammonium chloride, 12 weight percent propylene glycol, 5 weight percent ethanol.

EXAMPLE 3

Deviating from Example 2, 9 g of water are added in addition to the ethanol. The product obtained has a viscosity of 5,000 mPas and a water content of 3 weight percent. The betaine content of the solution is 75.4 weight percent.

EXAMPLE 4

Product A (1,000 g) is mixed with 73 g of water and 26 g of 1,2-propyleneglycol and worked up as in Example 1 with the addition of 28 g of ethanol. The product obtained has a viscosity of 900 mPas and a betaine content of 85 weight percent.

EXAMPLE 5

Monochloroacetic acid (103 g) and 1015 g of isopropanol are added to a 2 L glass flask, which is equipped with a stirrer, thermometer and reflux condenser. The mixture is heated slowly with stirring to 85° C. Potassium hydroxide pellets (73 g, 85%) are then added. The temperature is maintained at 85° C. until a homogeneous crystalline sludge has been formed. A total of 300 mL of isopropanol is then distilled off to remove the water of neutralization. Thereupon 300 g of the dimethylaminopropylamide of the hydrogenated coconut oil fatty acids are added. After reacting for 8 hours under reflux, the content of starting amide used as fallen to less than 10 weight percent, based on the betaine formed. The reaction mixture is cooled to room temperature and the precipitated potassium chloride is filtered off. In all, 75 g of dry potassium chloride are obtained, corresponding to 96% of the theoretically possible amount. The filtrate of 1094 g has a solids content of 35 weight percent.

The filtrate (1094 g) is mixed with 21 g of 1,2-propyleneglycol and subsequently freed from isopropanol by vacuum distillation. After cooling to 50° C., the reaction product (404 g) is mixed with 21 g of ethanol and cooled to 30° to 40° C.

The final product has a viscosity of 5,000 mPas at room temperature and the following composition: 88 weight percent betaine, 1 weight percent potassium chloride, 1 weight percent water, 5 weight percent 1,2-propyleneglycol, 5 weight percent ethanol.

EXAMPLE 6

Monochloroacetic acid (103 g), 300 g of the dimethylaminopropylamide of hydrogenated coconut oil fatty acids and 400 g of isopropanol are added to a 2 L glass flask, which is equipped, with a stirrer, thermometer, reflux condenser and dropping funnel. The reaction mixture is heated slowly with stirring to 85° to 90° C., at which time 124 g of a 50% aqueous potassium hydroxide solution are added dropwise at this temperature within a period of 1 hour. After this, the residual content of the amidamine used is less than 10 weight percent, based on the betaine formed.

After cooling, the product is diluted with 300 g of isopropanol and the precipitated potassium chloride is filtered off. A total of 78 g of dry potassium chloride are obtained, corresponding to 95% of the theoretically possible amount. The filtrate of 1149 g has a solids content of 33.7 weight percent.

21.5 g of 1,2-propyleneglycol is added to 1149 g of the filtrate and subsequently the isopropanol is removed by vacuum distillation. After cooling to 50° C., the reaction product (408 g) is additionally admixed with 21.5 g of ethanol and cooled down to 30°-40°.

The final product has a viscosity of 5,000 mPas at room temperature and the following composition: 88 weight percent betaine, 1 weight percent potassium chloride, 1 weight percent water, 5 weight percent 1,2-propyleneglycol, 5 weight percent ethanol.

The following Table shows the composition and viscosity of the solutions of Examples 1 to 6.

TABLE

| Composition | Example 1 | Example 2 | Example 3 | Example 4 | Example 5 | Example 6 |
|---|---|---|---|---|---|---|
| Betaine | 78.8% | 78.4% | 75.4% | 85% | 88% | 88% |
| NH₄Cl | 4.6% | 4.6% | 4.6% | 5% | — | — |
| KCl | — | — | — | — | 1% | 1% |
| Propylene glycol | 14.6% | 12% | 12% | 4.7% | 5% | 5% |
| Ethanol | 2% | 5% | 5% | 5% | 5% | 5% |
| Water | — | — | 3% | 0.9% | 1% | 1% |
| Viscosity (mPas) | 20,000 | 10,000 | 5,000 | 900 | 5,000 | 5,000 |

I claim:

1. A method for the preparation of a flowable and pumpable solution containing at least 70 weight percent of betaine of the following general formula

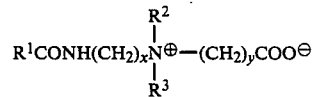

in which $R^1$ is the alkyl group of a fatty acid or a fatty acid mixture with an average of 6 to 18 carbon atoms, $R^2$ and $R^3$ are the same or different and represent an alkyl or a hydroxyalkyl group with 1 to 4 carbon atoms, x has a value of 2 or 3 and y a value of 1, 2, 3 or 4, said method comprising the steps of quaternizing at elevated temperature a compound of the general formula $R^1CONH(CH_2)_xNR^2R^3$ with the salt of a halogencarboxylic acid $X(CH_2)_yCOOMe$, in which X is halogen and Me is a monovalent cation, wherein (a) the $R^1$ group is selected so that the compound of the formula $R^1CONH(CH_2)_xNR^2R^3$ has a melting point of at the most 30° C., (b) said quaternization being carried out (b₁) with the potassium or ammonium salt of the halogencarboxylic acid X(CH₂)ᵧCOOH, (b₂) in an organic polar solvent, which contains at the most 20 weight percent of water, said polar solvent being a monovalent aliphatic alcohol having 2–4 carbon atoms, and wherein (c) after the quaternization, any water contained in the reaction mixture is distilled off azeotropically and the precipitated potassium or ammonium halides is removed, (d) whereupon the solvent is distilled off partly or completely, and (e) before, simultaneously with or after the distillation, the concentration of the betaine in the solvent or the solvent mixture is adjusted to at least 70 weight percent with an aliphatic dialcohol with 2–4 carbon atoms or a mixture of an aliphatic dialcohol and an aliphatic monoalcohol with 2 to 4 carbon atoms.

2. The method as defined in claim 1, wherein the quaternization is carried out in isopropanol or ethyl alcohol.

3. The method as defined in claim 1, wherein the betaine is dissolved pursuant to step (e) in propylene glycol or a mixture of propylene glycol and ethyl alcohol.

4. The method of claim 1, wherein $R^1$ is the alkyl group of a fatty acid having not more than 10 carbon atoms.

5. The method of claim 1, wherein $R^1$ is the alkyl group of a fatty acid mixture having on the average 12 carbon atoms.

6. A flowable and pumpable solution, containing a betaine of the general formula of claim 1 and having the composition 70 to 97.5 weight percent betaine 2 to 15 weight percent aliphatic diol with 2 to 4 carbon atoms 0.5 to 10 weight percent aliphatic monoalcohol with 2 to 4 carbon atoms 0 to 5 weight percent water.

7. A flowable and pumpable solution, containing a betaine of the general formula of claim 1 and having the composition 70 to 97.5 weight percent betaine 2 to 15 weight percent propylene glycol 0.5 to 5 weight percent ethanol 0 to 5 weight percent water.

8. A flowable and pumpable solution comprising at least 70 percent by weight of the betaine of claim 1 in an organic solvent.

9. The solution of claim 8, additionally comprising up to 5% by weight of water.

10. The solution of claim 8, wherein the organic solvent is a diol with 2–4 carbon atoms and a monoalcohol with 2–4 carbon atoms.

* * * * *